United States Patent [19]
Kaiser et al.

[11] 4,086,274
[45] Apr. 25, 1978

[54] N-(2-MERCAPTO-ETHYL)ALKANAMIDES FROM H₂S AND 2-H-2-OXAZOLINES OR 2-ALKYL-2-OXAZOLINES

[75] Inventors: Mark E. Kaiser; Peter W. Owen, both of Midland, Mich.

[73] Assignee: The Dow Chemical Company, Midland, Mich.

[21] Appl. No.: 743,888

[22] Filed: Nov. 22, 1976

Related U.S. Application Data

[63] Continuation-in-part of Ser. No. 589,322, Jun. 23, 1975, abandoned.

[51] Int. Cl.² .................. C07C 102/00; C07C 85/00
[52] U.S. Cl. ........................ 260/561 S; 260/307 G; 260/307 F; 260/558 S; 260/559 T; 260/562 S; 260/583 EE; 260/570.5 S
[58] Field of Search .......... 260/561 S, 307 G, 307 F, 260/558 S, 559 T, 562 S, 583 EE, 570.5 S

[56] References Cited
U.S. PATENT DOCUMENTS 3,414,620  12/1968  Bresson et al. ................... 260/584

OTHER PUBLICATIONS

Frump Chemical Reviews, 71, (1971), pp. 496–499.
Goldberg, J. Chem. Soc., 1948, pp. 1919–1926.
Fry, J. Org. Chem., 15, (1950), pp. 438–447.

*Primary Examiner*—Arthur P. Demers
*Attorney, Agent, or Firm*—L. Wayne White

[57] ABSTRACT

N-(2-mercaptoethyl)alkanamides are produced by reacting hydrogen sulfide with 2-H-2-oxazolines or 2-alkyl-2-oxazolines. For example, N-(2-mercaptoethyl)acetamide was prepared in excellent yields by incrementally adding 2-methyl-2-oxazoline to a stirred solution of hydrogen sulfide in methanol under autogeneous pressure at about 100° C.

15 Claims, No Drawings

N-(2-MERCAPTO-ETHYL)ALKANAMIDES FROM $H_2S$ AND 2-H-2-OXAZOLINES OR 2-ALKYL-2-OXAZOLINES

CROSS REFERENCE TO RELATED APPLICATION

This is a continuation-in-part of our copending application Ser. No. 589,322, filed June 23, 1975, now abandoned.

BACKGROUND OF THE INVENTION

The chemistry of oxazolines has been reviewed extensively in three major review articles: (1) Wiley et al., Chemical Reviews, Volume 44, 447 (1949); (2) Seeliger et al., Angew. Chem. International Addition, Volume 5, No. 10, 875 (1966); and (3) Frump, Chemical Reviews, 1971, Volume 71, 5483. Such review articles indicate that a wide variety of ring-opening reactions of oxazolines are known but suprisingly few reactions of hydrogen sulfide with oxazolines have ever been considered.

The reactions of certain 2-aryl-2-oxazolines with hydrogen sulfide were described, for example, by Goldberg et al., J. Chem. Soc., 1919(1948) and by Fry, J. Org. Chem. 15 438(1950). The first reaction was said to produce N-(2-hydroxyethyl)benzothioamide. The second reference utilized a different 2-aryl-2-oxazoline and obtained somewhat different results (i.e. a substituted N-(2-mercaptoethyl)benzamide).

Tomalia et al. (U.S. Pat. No. 3,670,046) taught that certain bisoxazolines react with bismercaptans or hydrogen sulfide to produce polymers.

Tomalia et al. also taught in U.S. Pat. Nos. 3,630,996; 3,723,451 and 3,746,691 that hydrogen sulfide reacts with certain 2-alkenyl-2-oxazolines to produce the corresponding bis(2-oxazolinylethyl)sulfides.

SUMMARY OF THE INVENTION

We have now discovered that 2-H-2-oxazolines and 2-alkyl-2-oxazolines react with hydrogen sulfide (preferably in liquid phase) to produce N-(2-mercaptoethyl)alkanamides. Such products form a known class of useful compounds having many members, all of which can be hydrolyzed with aqueous HCl to form a 2-mercaptoethylamine hydrochloride which has utility, when neutralized, as an epoxy curing agent, acid scavenger, chemical intermediate, etc.

DETAILED DESCRIPTION OF THE INVENTION

The reactants in the instant process are known classes of reactants. The 2-H-2-oxazolines and 2-alkyl-2-oxazolines correspond to the formula

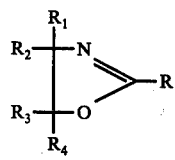

I in which R is hydrogen or an alkyl group and $R_1$–$R_4$ are hydrogen or inert organic groups (i.e. they are inert in the process). Preferably, R is an alkyl group of from 1 to about 18 carbon atoms and most preferably R is methyl or ethyl. $R_1$–$R_4$ are preferably hydrogen, lower alkyl ($C_1$–$C_6$), hydroxy-substituted lower alkyl, or phenyl. More preferably, $R_1$ and $R_2$ are hydrogen, methyl, ethyl or hydroxymethyl and $R_3$ and $R_4$ are each hydrogen. Most preferably, $R_1$–$R_4$ are each hydrogen.

Examples of suitable such 2-alkyl-2-oxazoline reactants include those of formula I having the values of R and $R_1$–$R_4$ set forth in Table 1, and the like.

Table 1

| R | $R_1$ | $R_2$ | $R_3$ | $R_4$ |
|---|---|---|---|---|
| H | H | H | H | H |
| $CH_3$ | H | H | H | H |
| $C_2H_5$ | H | H | H | H |
| $C_7H_{15}$ | H | H | H | H |
| $C_{11}H_{23}$ | H | H | H | H |
| $C_{17}H_{35}$ | H | H | H | H |
| $CH_3$ | $C_6H_5$ | H | H | H |
| $C_5H_{11}$ | $C_6H_5$ | H | H | $C_6H_5$ |
| $C_2H_5$ | $CH_3$ | H | H | H |
| $CH_3$ | $CH_3$ | $CH_3$ | H | H |
| $C_8H_{17}$ | $CH_2OH$ | $CH_2OH$ | H | H |
| $C_2H_5$ | $C_4H_9$ | H | H | $C_6H_5$ |
| $CH_3$ | H | H | $CH_3$ | $CH_3$ |
| $C_2H_5$ | H | H | H | $C_2H_5$ |

The 2-oxazolines used herein are normally prepared by reacting an alkanoic acid with an ethanolamine to form the corresponding acid/amine salt or amide which in turn is heated in the presence of an aluminum oxide catalyst to form the corresponding 2-alkyl-2-oxazoline product. This is a conventional process and is well documented in the literature.

Hydrogen sulfide is also a well known compound. It is a colorless gas at atmospheric conditions and is soluble in both water and alcohol. The solubility of hydrogen sulfide in alcohol is advantageous in the instant process.

The reaction may be conducted neat or in an inert organic solvent. By "inert" we mean inert in the instant process. Suitable such solvents include the lower alkanols and particularly methanol and combinations of such lower alkanols with conventional hydrocarbon solvents (e.g. benzene, toluene, etc.). We prefer to conduct the instant process neat or in methanol. Further, we prefer to conduct the reaction under substantially anhydrous conditions. The 2-oxazolines are susceptible to hydrolysis by water and essentially anhydrous conditions are therefore required to optimize product yield.

The stoichiometry of the reaction requires 1 mole of hydrogen sulfide per mole of 2-alkyl-2-oxazoline reactant. More or less than the stoichiometric amount of either reactant can be used, however. In fact, we prefer to use an excess of hydrogen sulfide to "force" the reaction to completion and maximize the product yield at the expense of by-products (i.e. bis(alkanamidoethyl) sulfides).

The order of addition or method of blending the reactants is not critical and may be varied to convenience. From a procedural standpoint, however, we have found it advantageous to add the hydrogen sulfide incrementally to a reaction vessel precharged with the oxazoline reactant. This manner of addition is also a convenient way of controlling the reaction temperature.

Substantially any reaction temperature of from about 20° to about 200° C can be used but we normally prefer to conduct the reaction at a temperature of from about 50° to about 150° C. At these temperatures, the reaction may be conducted under autogenous or superatmospheric pressures in conventional pressure equipment. The instant reaction is exothermic and normally will not require additional heat after the reaction is started. Indeed, we find it advantageous to conduct the reaction in equipment where the temperature can be controlled by cooling.

It has been observed that the reaction rate and product yields are lower when a reaction temperature in lower ranges are used (e.g. from about 20° to about 70°, or so). In these instances the product yields can be increased by warming the reaction mixture to the preferred temperature range (e.g. 100°–150° C). This post-heating step appears to cause at least one of the by-products (e.g. a hydroxyethyl thiocarboxamide) to thermally revert to the starting materials and/or rearrange to the desired product. The mechanism is not, however, firmly understood.

EXPERIMENTAL

The following examples will further illustrate the invention.

EXAMPLE 1

Preparation of N-(2-mercaptoethyl)acetamide

A 1-liter Parr pressure reactor was charged as follows: 192.2 g of anhydrous methanol and hydrogen sulfide (73.0 g; 2.142 moles; 7 percent excess) were admitted, and the stirred solution heated to 100° C. 2-Methyl-2-oxazoline (169.3 g; 1.989 moles) was then pumped into the sealed bomb through a check valve at ~2.5 g/minute rate. The temperature of the stirred solution rose to 111° C during addition and the pressure within the bomb dropped from 320 to 65 psig. The drop in pressure indicates conversion of $H_2S$. To insure complete conversion, the reactor was heated at this temperature for an additional 4 hours. During this post-heating period the bomb pressure remained constant indicating the reaction was essentially complete. The reaction mixture was cooled and volatiles removed therefrom under reduced pressure. Analysis of the remaining pot material by standard iodide/iodate titration (mercaptan functional group analysis) indicated 201.9 g of the desired amide, an 85.1 percent yield based on the oxazoline charged. Distillation under reduced pressure afforded at 92.6 percent recovery of a water-white, viscous liquid boiling at 125° C/0.9 mm Hg. Bis-(acetamidoethyl)sulfide was produced as a by-product in amounts which essentially accounted for the remainder of the reactants.

N-(2-mercaptoethyl)propionamide was produced in similarly good yields under essentially the same process conditions.

EXAMPLE 2

Preparation of N-(2-mercaptoethyl)propionamide

2-Ethyl-2-oxazoline (496.4 g; 5.01 moles) was charged to a 1-liter stainless steel Parr reactor, equipped with a stirrer, heating means, and a "dip tube" designed to introduce the gaseous reactant $H_2S$ below the surface of the liquid oxazoline. The oxazoline was warmed to 70° C and hydrogen sulfide (189.5 g, 5.56 moles) was added to the reaction vessel through the dip tube at a rate of 3.7 g per minute. The temperature was maintained at 70°–75° C during the addition of $H_2S$ and for an additional 4.3 hours after the addition was complete. The reaction mixture was subsequently heated at 150° C for 5 hours. After this post-heating step, the reaction mixture was cooled to 85° C, excess $H_2S$ vented to a caustic scrubber, and nitrogen bubbled through the remaining liquid reaction mixture to remove residual $H_2S$. Analysis of the clear, brown liquid product (653.7 g) thus obtained indicated that the desired product, N-(2-mercaptoethyl)propionamide, was produced in 86.8 percent of theoretical yield, based on the oxazoline charged. The desired product was recovered from the crude product by use of a falling film still. The desired product was thus obtained as a water white liquid containing a minor amount (less than 5 percent) of 2-ethyl-2-thiazoline. The presence of this thiazoline is not a disadvantage since it also hydrolyzes under the conditions set forth below to form the mercaptoethylamine hydrochloride.

UTILITY

Preparation of Mercaptoethylamine Hydrochloride

An aliquot of the N-(2-mercaptoethyl)acetamide from Example 1 above (119.2 g; 1.00 mole) and 19.5 percent aqueous HCl (205.6 g; 1.10 mole) were combined in a reaction vessel equipped with a magnetic stirrer and reflux condensor. The reaction mixture was heated to reflux (approximately 107° C) for about 4 hours, under a nitrogen blanket. Volatiles were then removed from the reaction mmixture under vacuum leaving a viscous, slightly yellow pot liquid which crystallized to a white solid upon cooling. The crystalline material (114.0 g) was identified by its nuclear magnetic resonance and infrared spectra as mercaptoethylamine hydrochloride. This salt is an item of commerce having many utilities, not the least of which is its use as a chemical intermediate in the synthesis of various pharmaceuticals. This salt can also be neutralized with a base (e.g., NaOH) and used as an epoxy curing agent in epoxy resins. Both the mercapto group and amino group are reactive with the epoxy moiety. See "Handbook of Epoxy Resins" by Lee and Neville, McGraw-Hill Book Company (1967). Further, the neutralized salt can obviously be used as an acid scavenger to inhibit acid corrosion, etc. Other mercaptoethylamines can be similarly used.

We claim:

1. A process of preparing a N-(2-mercaptoethyl)alkanamide comprising reacting by contacting under essentially anhydrous conditions (a) a 2-H-2-oxazoline or a 2-alkyl-2-oxazoline of the formula:

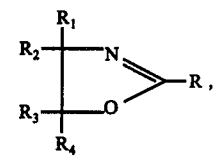

in which R is hydrogen or alkyl and $R_1$–$R_4$ are each independently hydrogen, lower alkyl, hydroxy-substituted lower alkyl or phenyl, with (b) hydrogen sulfide.

2. The process defined by claim 1 in which the molar ratio of (b):(a) is at least 1.

3. The process defined by claim 1 in which the reaction is conducted in an inert organic solvent.

4. The process defined by claim 3 in which the inert organic solvent is a lower alkanol of from 1 to 4 carbon atoms.

5. The process defined by claim 4 in which the inert organic solvent is methanol.

6. The process defined by claim 1 in which the reaction is conducted neat.

7. The process defined by claim 1 in which R is alkyl of from 1 to about 18 carbon atoms.

8. The process defined by claim 7 in which $R_1$ and $R_2$ are hydrogen, methyl, ethyl or hydroxy methyl and $R_3$ and $R_4$ are each hydrogen.

9. The process defined by claim 8 in which $R_1$-$R_4$ are each hydrogen and R is methyl or ethyl.

10. The process defined by claim 1 in which the reaction is conducted at a temperature of from about 20° to about 200° C.

11. The process defined by claim 10 in which the reaction temperature is from about 50° to about 150° C.

12. The process defined by claim 1 in which the process is conducted neat under autogenous or superatmospheric pressure.

13. The process defined by claim 2 wherein (a) is 2-methyl-2-oxazoline or 2-ethyl-2-oxazoline and wherein the reaction is conducted neat or in a methanol solution at a temperature of from about 50° to about 150° C under autogenous or superatmospheric pressure.

14. The process defined by claim 1 in which R is hydrogen.

15. The process defined by claim 1 which comprises the additional step of hydrolyzing the N-(2-mercaptoethyl)alkanamide with an aqueous protic acid to thereby form a 2-mercaptoethylamine.

* * * * *